United States Patent [19]
Krogseng et al.

[11] B 3,982,536
[45] Sept. 28, 1976

[54] BALLISTIC INOCULATION OF ANIMALS AND PROJECTILE THEREFOR

[75] Inventors: Gerald P. Krogseng, Oakdale; Fred R. Paul, Jr., Burnsville, both of Minn.

[73] Assignee: Minnesota Mining and Manufacturing Company, St. Paul, Minn.

[22] Filed: Nov. 15, 1974

[21] Appl. No.: 524,121

[44] Published under the second Trial Voluntary Protest Program on February 3, 1976 as document No. B 524,121.

[52] U.S. Cl. ............................. 128/260; 128/217; 128/271; 128/264
[51] Int. Cl.² ................. A61M 5/00; A61M 5/18; A61M 31/00
[58] Field of Search ........... 128/260, 264, 271, 217; 424/19, 21; 102/92 R, 92.4

[56] References Cited
UNITED STATES PATENTS

| 251,355 | 12/1881 | Gibbs | 128/271 |
|---|---|---|---|
| 979,993 | 12/1910 | O'Byrne et al. | 102/92 |
| 2,584,166 | 2/1952 | Stevenson et al. | 128/271 X |
| 2,617,359 | 11/1952 | VanHorn et al. | 102/92 |
| 2,854,925 | 10/1958 | Crockford et al. | 102/92 |
| 3,122,475 | 2/1964 | Schaeppi | 128/271 |
| 3,344,711 | 10/1967 | Mawhinney et al. | 102/92.4 |
| 3,429,263 | 2/1967 | Snyder et al. | 102/92 R |
| 3,520,299 | 7/1970 | Lott et al. | 128/217 |
| 3,538,214 | 11/1970 | Polli et al. | 424/19 |
| 3,616,758 | 11/1971 | Komarov | 102/92 |
| 3,857,932 | 12/1974 | Shepherd | 424/19 |

OTHER PUBLICATIONS

"Final Report, Ballistic Delivery of Biological Reagents", Sept. 15, 1973, Sensory Systems Laboratory, Animal & Plant Health Inspection Service, U.S. Dept. of Agriculture, Contract 12–16–140–213–91, By Howard A. Baldwin et al.

*Primary Examiner*—Aldrich F. Medbery
*Attorney, Agent, or Firm*—Alexander, Sell, Steldt & DeLaHunt

[57] ABSTRACT

Ballistic projectile containing an antigen and method for inoculating animals comprising the non-lethal, ballistic implantation of a projectile containing antigen totally within a living animal. Following implantation, the antigen is released in situ in the animal in response to the fluids and cells of the animal body.

**

BALLISTIC INOCULATION OF ANIMALS AND PROJECTILE THEREFOR

The present invention relates to the inoculation of living animals. More particularly the invention relates to a ballistic projectile containing an antigen and a method for conveniently delivering the antigen to the animal from a remote location, which method comprises the non-lethal, ballistic implantation of a projectile containing an antigen totally within a living animal body and the release of the antigen in situ in the animal body.

The vaccination of domestic and wild animals is normally performed by injection of a vaccine in liquid form from a syringe having a sharp, smooth, small diameter needle for minimal wounding. This method of vaccination requires the capture and confinement of the animals so that the vaccination can be accomplished, a difficult and time consuming process, particularly with wild animals. Moreover, multiple inoculations are sometimes necessary to achieve a desired effect, due to the inability of the animal body to efficiently assimilate the amount of inoculant required in a single application.

An important disadvantage in administering liquid vaccines by syringe involves the preparation of the vaccine. The vaccine is manufactured in a concentrated, freeze-dried form and must be reconstituted prior to use of the vaccine. The dry vaccine is more stable than the liquid form and can be shipped and stored under refrigerated conditions, usually less than 4° C., until reconstituted for use.

When prepared for use in the animal, the user reconstitutes the vaccine with a sterile liquid provided by the manufacturer. The reconstituted vaccines must be maintained in a cool environment (e.g., ice-bath temperatures) to insure the quality and activity of the vaccine. While the quality of the dried vaccine can be carefully controlled by the manufacturer, the quality and dosage accuracy of the reconstituted vaccine is limited by the care exercised by the ultimate user.

In practice, several animals may be inoculated with the same needle and disease can be actually transmitted to healthy animals by these conventional procedures.

Various methods of increasing the immune response to injected antigens are known. Decreasing the solubility of antigens by administering them as emulsions in various oily materials or adsorbed onto poorly soluble materials, such as aluminum hydroxide, increases the residence time of the antigens in the body and does produce an increased immune response. However, these emulsions and suspensions are difficult to administer by needle and syringe, and undesirable tissue reactions may also occur.

Bacterial cells or extracts can also be added to the antigen preparation as adjuvants to provoke an increased immune response. Because adjuvants are not passive agents, their use is limited, since the animal may become sensitive to the adjuvant or the response to the adjuvant may be undesirable. For example, mycobacteria cannot be used as adjuvants for cattle vaccination since the animals become tuberculin positive.

Multiple injections of antigen spaced over several weeks or months, i.e. booster shots, will usually result in an increased antibody production compared to a single injection. These multiple injections are uneconomical and time consuming.

According to the present invention, there is provided a ballistic projectile containing an antigen and adapted to release the antigen in situ in a living animal body.

One aspect of the invention relates to a ballistic projectile capable of penetrating the epidermal covering of a living animal body, lodging totally within the body, and presenting an antigen to the living body, the antigen being released and assimilated by the body fluids and cells surrounding the implanted projectile.

A further aspect of the invention relates to a unique method of inoculating living animals, particularly cattle and other domestic livestock, wherein a projectile containing an antigen is ballistically implanted totally within a living animal body, thereafter releasing the antigen into the animal body in response to the fluids and cells of the animal body. This method of inoculation provides several advantages. The ballistic method of implantation using the projectiles disclosed herein eliminates the need for actual human contact with the living animals in order to effect inoculation. The projectiles used in the ballistic inoculation are also adapted to contain antigens in a stabilized, dried form until released and absorbed in situ by the animal's fluids and cells and preparation of the antigen-containing ballistic projectiles can take place under sterile, controlled conditions and accurate dosages provided as desired. The full dosage is then available to the animal and can not be partially "dribbled" away as can happen with faulty syringe techniques.

Furthermore, tests on beef cattle such as Angus, Hereford, Shorthorn, and the like, following inoculation with Infectious Bovine Rhinotracheitis (IBR) vaccine according to the present invention, suggests that the effect of the antigen, i.e., the animals' response to the antigen, is greatly increased when the animals are inoculated by the present method compared to conventional syringe inoculations. It is not clearly understood why this surprising effect is achieved using a ballistic inoculation. However, it is believed the trauma at the wound site caused by ballistic implantation may stimulate the defense mechanisms of the body, thereby provoking an increased immune response and heightened antibody production.

Ballistic inoculation of beef cattle with antigen has been found particularly effective. In a preferred embodiment, a small ballistic projectile having a conical nose and a cavity opening to the rear of the projectile is loaded with a given dose of antigen, preferably a freeze dried vaccine. The projectile is then propelled into the flesh of the animal from a distance, using an air powered rifle. The projectile lodges under the epidermal covering of the animal with the implant site showing a minimal amount of swelling or hematoma. On lodging within the animal, the body fluids and cells of the animal surrounding the projectile rehydrate or otherwise release and absorb the antigen which then activates the animal's defense mechanisms, whereby the desired antibodies are produced rendering the animal immune to specific diseases.

The present invention can be illustrated with reference to the drawings wherein several embodiments of projectiles useful in the present invention are shown.

Figure 1:
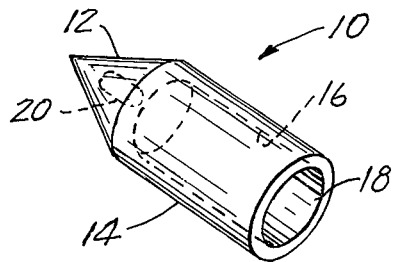
FIG. 1 is a perspective view of one embodiment of a ballistic projectile adapted to receive, carry and release an antigen.

Referring to FIG. 1, there is shown a cylindrical, ballistic projectile 10 comprising a conical nose 12 and annular walls 14 defining a generally cylindrical cavity 16 with an opening 18 at the base of the projectile. A ballast shown generally at 20 may optionally be included to modify the in-flight characteristics of the ballistic projectile. This projectile is particularly suited to accept, retain, and release an antigen, as will be more fully described hereinafter. Projectile 10 can be made of any material which is capable of being projected with sufficient force to penetrate a living animal body and which will maintain its integrity, e.g. will not shatter, on impacting and entering the animal body. Any of the numerous biomedically approved plastics can be used with advantage and can be selected from among those which are either soluble or insoluble in the animal body. Exemplary of useful insoluble materials are the synthetic organic polymers such as the polyolefins, e.g., polyethylene and polypropylene; polysiloxane; polyamides, such as nylon; fluorinated hydrocarbon resins; ABS polymers (acrylonitrile-butadienestyrene polymers) and the like. A suitable class of polymers which are soluble in animal bodies, e.g. cattle, are the cellulose derivatives such as hydroxypropyl cellulose, available commercially from the Hercules Powder Co. under the tradename "Klucel". The use of soluble projectiles can be particularly advantageous since after implant the projectile will be solubilized in and eliminated from the animal's body, eliminating the need to retrieve the projectile.

Figure 2:
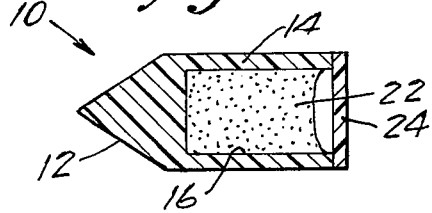
FIGS. 2 and 3 are cross sectional views of alternate embodiments of projectiles capable of carrying and releasing an antigen.

FIG. 2 shows a projectile 10 with conical nose portion 12 and annular walls 14 defining a cavity 16 which contains antigen 22 therein. Sealing cap 24 is optional and can be added for additional protection of the projectile contents during storage and launching if desired. Cap 24 can be made of a soluble material whereby the cap can dissolve in the animal body after being implanted and expose the antigen 22 to the animal body fluids.

Alternatively, cap 24 of FIG. 2 can be removably fastened to the projectile 10 in which case the cap can be removed prior to launching or can be constructed to separate from the projectile during launching, in flight, or at impact prior to entering the animal body. A preferred embodiment comprises a cap 24 spot fastened to projectile 10 by heat sealing or by adhesive means (not shown) whereby the force exerted on cap 24 during launching causes the cap to bow or buckle an amount sufficient to fracture the adhesive bond and release the cap after leaving the launching instrument, e.g., a compressed air gun. As noted above, the body of projectile 10 can be made of a soluble or insoluble material, as desired. As can be appreciated, the projectile 10 may contain any number of compartments or cells in various forms which cells may contain antigens which are alike or different. Thus, an embodiment wherein a plurality of cells are distributed longitudinally in the cavity and opening at the base of the projectile is also contemplated whereby a plurality of antigens contained therein could be released simultaneously.

Figure 3:
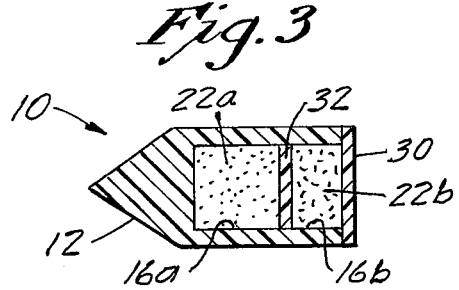

A further embodiment is shown in FIG. 3 wherein cavity 16 is divided into compartments 16a and 16b by soluble end cap 30 and seal 32. Antigens 22a and 22b are shown contained within compartments 16a and 16b and can be the same or different. End cap 30 and seal 32 can be chemically similar or different, having similar or different solubilities in animal body fluids. This embodiment provides a convenient means for releasing consecutive doses of antigens in situ at spaced intervals. Materials which may be used for the end cap 30 or seal 32 are any of the materials which are solid at room temperature and which will melt, solubilize, degrade or otherwise mobilize to release the contents sealed therein. Cap 30 may also be releasably adhered to projectile 10 as is cap 24 described in FIG. 2 above.

As illustrated in the drawings, the projectiles of the present invention have been shown with recessed cavities generally cylindrical in nature, opening at the base of the projectile and defined by annular projectile walls. However, other recesses or cavities which vary as to location or shape can be utilized with advantage. Thus, one or more cavities which are rectangular or triangular rather than rounded are contemplated as well as cavities which are straight, twisted, or constricted. Moreover, the cavities need not be provided with an opening at the base of the projectile and they may extend transversely of the projectile with access at the sides or other portion of the projectile.

The projectiles of the present invention are adapted to be implanted into living animal bodies by ballistic means such as by launching or "shooting" the projectiles from a convenient distance with small arms or other launching devices powered by expanding gas means such as explosive charges or compressed gases, preferably air. When properly launched, the projectiles will penetrate a living animal body in a non-lethal manner and come to rest within the body. The depth of penetration of the projectile can be controlled by balancing the relationship between the mass of the projectile and the velocity of the projectile at impact. The design of the projectile can vary, and conventional designs useful herein are known in the art. The projectile design can be varied to achieve the desired degree of penetration into the body as well as to achieve the desired performance with respect to a wide range of impact velocities and a wide range of animals. Many texts are available to those skilled in the ballistics art which teach operative designs for the ogival and other portions of the projectile. See, for example, Hayes, "Elements of Ordnance", John Wiley and Sons, Inc., New York. It is generally preferred that the projectile have an elongated body with a tapered nose portion which may be conical as shown in the accompanying drawings, rounded or the like. A projectile design similar to that shown in the FIGURES of the drawings has been found effective for the intramuscular implantation of a 0.25 caliber projectile into the flanks and necks of beef cattle at a distance of about 20 to 40 feet (6–12 meters). The projectile should be capable of penetrating into and through the body tissue to the desired depth for maximum effectiveness depending on whether subcutaneous or intramuscular treatment is desired. The point at which entry into the living body is effected can readily be determined for maximum effectiveness utilizing minimum force.

Antigens, i.e. materials which when administered to an animal will cause the formation of antibodies by the animal, such as the viruses, bacteria and toxoids are well known in the art and are useful in the practice of this invention. Particularly useful viruses and bacteria are the vaccines and bacterins, i.e. preparation of viruses or bacteria (live or killed) used to protect against a specific disease.

Vaccines can comprise either the killed or living virus and can be wild (pathogenic) or attenuated. A preferred vaccine prepared from living, attenuated virus is the previously mentioned IBR vaccine. Yet another useful vaccine is the hoof and mouth vaccine prepared from killed, wild virus.

The bacterins can comprise living or killed bacteria which may be wild or attenuated. Exemplary of the bacterins prepared from live bacteria is the anthrax bacterin prepared from anthrax spores, a live, attenuated bacteria. Bacterins prepared from killed bacteria are exemplified by the black leg Clostridium, a killed, wild bacteria.

As mentioned above, toxoids can also be conveniently administered by the practice of the present invention. For example, equines may be inoculated with a tetanus toxoid to protect against tetanus. Other antigens which may not be considered viruses, bacteria, or toxoids, e.g. the allergenics, such as the pollens, which may produce antibodies in living animals, are also suitable for use in the present invention.

In the practice of the invention, the antigens are generally prepared in liquid form, deposited in the cavity of the projectile and dried, preferably by lyophilization. Alternatively, the antigens can be sealed or otherwise contained in the projectile in liquid form, but the dry form is preferred since the antigens are more stable in that form.

After loading the projectiles with antigen, the projectiles can be stored at reduced temperatures, e.g. less than about 20° C. and preferably about 4° C., for extended periods of time until used for inoculation.

When the projectile has been ballistically implanted into the animal body, the fluids and cells of the body act to release and/or rehydrate the antigen which then activates or stimulates the animal's defense mechanisms provoking an immune response and increased antibody production.

As noted previously, the projectile is adapted to penetrate and lodge within the animal body in an area which is effective to release the antigen and which does not harm the animal. For example, the flanks and neck muscles of cattle are ideal inoculating areas for many antigens. The penetration of the projectile necessarily causes some minimal wounding of the animal, but the wound is non-lethal and the trauma is slight. Experience with beef cattle has shown that bleeding from the projectile entry site is minimal, generally showing only a small circular spot of blood about 10 mm in diameter on the hide surface when a .25 calibre projectile is used. The implant sites will heal within a few days without any overt sign of infection, and unless specifically marked, locating the wound site is difficult. Surgical removal of the projectiles several days after implantation revealed no abscesses or gross inflamation surrounding the projectiles.

Though the effects are minimal, the slight trauma produced at the wound site by the ballistic implantation appears to be advantageous in the practice of the present invention since this trauma apparently stimulates antibody production in some manner causing an increased immune response compared to antigens applied by conventional means, e.g. in liquid form from syringes.

A preferred antigen-containing, ballistic projectile suitable for the vaccination of cattle according to the present invention is prepared by sterilizing, in ethylene oxide, a polypropylene projectile about 0.5 inch (1.25 cm) long, 0.25 inch (0.6 cm) in diameter, and having a conical nose portion. The projectile preferably has a cavity in its base sufficiently large to contain 0.05 ml of a liquid such as water. A typical sterilization program would involve exposure of the projectile to a 1200 mg/liter ethylene oxide atmosphere for 100 minutes at 60° C., followed by removal of the residual ethylene oxide under a vacuum of 2 mm Hg for about 18 hours at 60° C.

The sterilized projectile is then loaded with an antigen. A useful antigen for cattle is a modified (attenuated) live virus vaccine such as Infectious Bovine Rhinotracheitis (IBR) vaccine, which is available commercially from Anchor Laboratories, Inc. under the trade name "Anchor IBR-VAC". Typically, a (10-dose) vial of the vaccine is reconstituted with a 0.5 ml of sterilized water. The vaccine vial is rotated slowly to thoroughly wet the contents and allowed to stand 30 minutes on ice. Samples of 0.05 ml each are removed using sterile, disposable 0.05 ml capillary pipettes. The pipette contents are each transferred to separate tubes containing one milliliter of sterile water, rinsing the pipette with the receiving fluid. The samples are then assayed for virus titer by standard laboratory techniques such as the serum neutralization or plaque reduction methods, which procedures are outlined in "Recommended Standard Laboratory Techniques for Diagnosing Infectious Bovine Rhinotracheitis, Bovine Virus Diarrhea, and Shipping Fever (Parainfluenza-3)", Committee for Recommended Standard Techniques for Diagnosing Bovine Respiratory Disease, Proceedings of the 75th Annual meeting, U.S. Animal Health Association (1971).

The cavities of the previously sterilized projectiles are each loaded with 0.05 ml of the vaccine solution. The vaccine is then frozen at about −78° C and lyophilized. After lyophilization, the projectiles are placed in individual sterile, marked tubes and stored at about 4° C. until used for vaccination.

If desired, the liquid vaccine can be absorbed in or absorbed on appropriate substrates such as sterile blotter paper, a fibrous material such as a cotton wad, or other compatible sterile substrate from which the vaccine can be rehydrated or otherwise released while in the animal body.

Yet another means of carrying the vaccine in the projectile is to seal the vaccine in a release-sustaining matrix as disclosed in copending application Serial No. 497,462 filed Aug. 14, 1974, entitled "Ballistic Animal Implant", the disclosure of which is hereby incorporated by reference. A convenient method of providing the projectiles with a sustained release vaccine comprises reconstituting the vaccine with a 5% aqueous solution of hydroxypropyl cellulose binder. Lyophilizing this vaccine solution in the projectile cavity provides a vaccine sealed in a body-fluid-soluble, solid matrix which slowly releases the vaccine in response to the animal body fluids.

A further optional feature comprises the use of a removable cap to secure or protect the contained antigen up to and optionally including the time of launching the projectile as described previously with respect to the embodiment shown in FIG. 2.

The vaccine-containing projectiles prepared as described above can be used to inoculate beef cattle against Infectious Bovine Rhinotracheitis by ballistically implanting the projectile intramuscularly in the cattle, preferably in the neck muscles of the cattle. For example, the projectiles described above can be propelled with a 0.25 calibre air powered rifle at the large neck muscle in the upper portion of the neck of the cattle from a distance of about 20 feet (6 meters). The projectiles exit the muzzle of the air rifle with a muzzle velocity of about 900 feet per second (275 meters/sec) and will penetrate the hide on the necks of the cattle and lodge in the muscle at a depth of about 1 to 2 inches (2.5 – 5 cm) beneath the skin, thereafter releasing the antigen contained therein.

To determine the effect of the vaccine inoculation on the cattle, blood samples are taken from the cattle prior to ballistic implantation of the vaccine-containing projectiles and periodically after implant. The blood samples are assayed for IBR virus-neutralizing antibody by a serum neutralization technique referred to previously herein. By the 14th to the 21st day following implantation, significant titers of virus neutralizing antibody are noted at levels which are sufficient to protect the cattle from IBR challenge.

Beef cattle inoculated with IBR vaccine according to the present invention will show a surprisingly increased immune response when compared with cattle inoculated in the conventional manner. This can be evidenced by visual observation of cattle which have been challenged by exposure to IBR virus as well as by antibody titers of the exposed animals. The increased response produced by ballistic implantation of the antigen is particularly manifested by higher antibody counts than produced by conventional vaccination techniques and/or by a greater percentage of the animals of a given group reaching a protective level of antibody count than would be achieved by conventional syringe vaccination.

What is claimed is:

1. A ballistic implant shaped for penetrating the epidermal covering of a living animal body and lodging totally within the tissues of the animal body, the implant consisting essentially of a biologically compatible polymer body and an antigen contained within the polymer body in a manner permitting release of said antigen in response to the fluids and cells of the living animal body.

2. A ballistic implant according to claim 1 wherein said antigen is contained within a cavity opening to the rear of said polymer body.

3. A ballistic implant according to claim 2 wherein said cavity is sealed by a removable cap.

4. A ballistic implant according to claim 1 which includes ballast means within the polymer body.

5. A ballistic implant according to claim 1 wherein said antigen is in a solid form.

6. A ballistic implant according to claim 1 wherein said polymer body is soluble in the fluids and cells of said living animal body.

7. A ballistic implant according to claim 6 wherein said antigen is distributed throughout the soluble polymer body.

8. A ballistic implant according to claim 6 wherein said soluble polymer body comprises hydroxypropyl cellulose.

9. A method of inoculating living animal bodies with an antigen, said method comprising ballistically implanting totally within the tissues of said animal body a ballistic shaped implant consisting essentially of a biologically compatible polymer body and an antigen contained within the polymer body whereby said antigen is released in situ in said animal body in response to the fluids and cells of said animal body.

10. A method according to claim 9 wherein said antigen is selected from the group consisting of vaccines, bacterins and toxoids.

11. A method according to claim 9 wherein said antigen is in a solid form.

12. A method according to claim 9 wherein said polymer body is soluble in the fluids and cells of said living animal body.

13. A method according to claim 12 wherein said polymer body comprises hydroxypropyl cellulose.

* * * * *